(12) United States Patent
Muller et al.

(10) Patent No.: US 8,062,665 B2
(45) Date of Patent: Nov. 22, 2011

(54) 3'-[(2Z)-[1-(3,4-DIMETHYLPHENYL)-1,5-DIHYDRO-3-METHYL-5-OXO-4H-PYRAZOL-4-YLIDENE]HYDRAZINO]-2'-HYDROXY-[1,1'-BIPHENYL]-3-CARBOXYLIC ACID BIS-(MONOETHANOLAMINE)

(75) Inventors: Francis X Muller, King of Prussia, PA (US); Shivakumar G Kapsi, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/607,320

(22) Filed: Oct. 28, 2009

(65) Prior Publication Data
US 2010/0047347 A1 Feb. 25, 2010

Related U.S. Application Data

(63) Continuation of application No. PCT/US2007/074918, filed on Aug. 1, 2007.

(60) Provisional application No. 60/947,731, filed on Jul. 3, 2007, provisional application No. 60/915,761, filed on May 3, 2007.

(51) Int. Cl.
A61K 9/20 (2006.01)
A61K 31/4152 (2006.01)
C07D 231/38 (2006.01)
(52) U.S. Cl. ........................ 424/465; 514/404; 548/367.4
(58) Field of Classification Search .................. 424/465; 514/404; 548/367.4
See application file for complete search history.

(56) References Cited

U.S. PATENT DOCUMENTS

| | | |
|---|---|---|
| 851,444 A | 4/1907 | Shulthess |
| 2,809,963 A | 10/1957 | Hanhart |
| 2,950,273 A | 8/1960 | Pelz |
| 3,366,619 A | 1/1968 | DeLucia |
| 4,435,417 A | 3/1984 | Toja et al. |
| 4,510,149 A | 4/1985 | Cozzi et al. |
| 4,582,831 A | 4/1986 | Robertson |
| 4,686,285 A | 8/1987 | Pedrazzi |
| 4,880,788 A | 11/1989 | Moake et al. |
| 4,948,900 A | 8/1990 | Iijima et al. |
| 5,326,776 A | 7/1994 | Winn et al. |
| 5,482,546 A | 1/1996 | Eida et al. |
| 5,532,202 A | 7/1996 | Yoshida |
| 5,622,818 A | 4/1997 | Kapp et al. |
| 5,669,967 A | 9/1997 | Hays |
| 5,746,821 A | 5/1998 | Hays |
| 5,760,038 A | 6/1998 | Murugesan et al. |
| 5,932,546 A | 8/1999 | Barrett et al. |
| 6,214,813 B1 | 4/2001 | Zhang et al. |
| 6,238,442 B1 | 5/2001 | Schumacher et al. |
| 6,248,871 B1 | 6/2001 | Ebenezer et al. |
| 6,280,959 B1 | 8/2001 | Gleason et al. |
| 6,436,915 B1 | 8/2002 | Zhang et al. |
| 2001/0044474 A1 | 11/2001 | Curatolo et al. |
| 2003/0060453 A1 | 3/2003 | Zhang et al. |
| 2004/0063764 A1 | 4/2004 | Takemoto et al. |
| 2004/0082626 A1 | 4/2004 | Takemoto et al. |
| 2008/0286865 A1 | 11/2008 | Erickson-Miller et al. |
| 2009/0048318 A1 | 2/2009 | Erickson-Miller et al. |
| 2009/0143453 A1 | 6/2009 | Erickson-Miller et al. |
| 2009/0298179 A1 | 12/2009 | Erickson-Miller et al. |

FOREIGN PATENT DOCUMENTS

| | | |
|---|---|---|
| DE | 193350 | 11/1904 |
| DE | 1046220 | 12/1958 |
| EP | 0 638 617 | 8/1994 |
| EP | 1 207 155 | 7/2000 |
| EP | 1 253 142 | 1/2001 |
| EP | 1 104 674 | 6/2001 |
| GB | 826207 | 7/1956 |
| GB | 779 880 | 7/1957 |
| JP | 2002-371213 | 12/2002 |
| WO | WO 93/17681 | 9/1993 |
| WO | WO 94/12200 | 6/1994 |
| WO | WO 94/26709 | 11/1994 |
| WO | WO 96/40750 | 12/1996 |
| WO | WO 98/46606 | 10/1998 |
| WO | WO 99/11262 | 3/1999 |
| WO | WO 99/15500 | 4/1999 |
| WO | WO 00/35446 | 6/2000 |
| WO | WO 00/68222 | 11/2000 |
| WO | WO 01/77080 | 1/2001 |
| WO | WO 01/07423 | 2/2001 |
| WO | WO 01/17349 | 3/2001 |
| WO | WO 01/21180 | 3/2001 |
| WO | WO 01/34585 | 5/2001 |
| WO | WO 01/77108 | 10/2001 |
| WO | WO 01/89457 | 11/2001 |
| WO | WO 02/59099 | 1/2002 |
| WO | WO 02/59100 | 1/2002 |
| WO | WO 02/49413 | 6/2002 |

(Continued)

OTHER PUBLICATIONS

Leuner et al. European Journal of Pharmaceutics and Biopharmaceutics 2000, 50, 47-60.*
Shekunov et al. Pharmaceutical Research 2007, 24(2), 203-227.*
Lachman et al. The Theory and Practice of Industrial Pharmacy (3rd Ed.) 1986, Lea & Febiger (Pub.), Chapter 11 pp. 293-345.*
Jivraj et al. PSTT 2000, 3(2), 58-63.*
M.C. Gohel J. Pharm. Pharmaceut. Sci. 2005, 8(1), 76-93.*
Skelly et al. Pharmaceutical Research 1993, 10(2), 313-316.*
J.A. McCarty, American Pharmaceutical Review 2004, 7(1), 94-100.*
F.M. Etzler American Pharmaceutical Review, 2004 7(1), pp. 104-108.*
M.M. De Villiers J. of Pharm. & Biomedical Analysis 1995, 13(3), 191-198.*

(Continued)

Primary Examiner — Jason M Nolan
(74) Attorney, Agent, or Firm — Wayne J. Dustman; Edward R. Gimmi

(57) ABSTRACT

Disclosed are novel pharmaceutical compositions containing 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) (eltrombopag olamine) and processes for preparing the same.

12 Claims, 2 Drawing Sheets

FOREIGN PATENT DOCUMENTS

| WO | WO 02/057300 | 7/2002 |
|---|---|---|
| WO | WO 02/085343 | 10/2002 |
| WO | WO 03/045379 | 6/2003 |
| WO | WO03/074550 | 9/2003 |
| WO | WO03/098992 | 12/2003 |
| WO | WO 03/103686 | 12/2003 |
| WO | WO 2004/054515 | 7/2004 |
| WO | WO 2004/096154 | 11/2004 |
| WO | WO 2005/041867 | 5/2005 |
| WO | PCTUS2007074918 | 8/2007 |
| WO | WO2008/101141 | 8/2008 |
| WO | WO2008/136843 | 11/2008 |
| WO | WO2009/043883 | 5/2009 |

OTHER PUBLICATIONS

Yamazaki, et al., Database HCAPLUS, AN 1995: Abstract, 196968.
A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Duffy, et al., J. Med. Chem., 2001, vol. 44, No. 22, Abstract No. XP002197261.
Bartley, et al., Cell, 1994, vol. 77, pp. 1117-1124.
Olszewski, et al., Database CAPLUS on STN, 1995, Chem. Abstracts, No. 122:81695.
Olszewski, et al., J. Org. Chem., 1994, vol. 59, pp. 4285-4296.
Lamb, et al., Nucleic Acids Research, 1995, vol. 23, No. 16, pp. 3283-3289.
Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Shiotsu, et al., Experimental Hematology, 1998, vol. 26, pp. 1195-1201.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Kuter, et al., Seminars in Hematology, Apr. 2000, vol. 37, No. 2, pp. 41-49.
Ballestrero, et al., Oncology, 2000, vol. 59, pp. 7-13.
Sawai, et al., Journal of Leukocyte Biology, Jul. 2000, vol. 68, pp. 137-143.
Vigon, et al., Proc. Natl. Acad. Sci. USA, Jun. 1992, vol. 89, pp. 5640-5644.
Laurenz, et al., Comp. Biochem Physiol., 1997, vol. 116A, No. 4, pp. 369-377.
Metcalf, et al., Nature, Jun. 16, 1994, vol. 369, pp. 519-520.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Sauvage, et al., Nature, Jun. 16, 1994, vol. 369, pp. 533-538.
Wendling, et al., Nature, Jun. 16, 1994, vol. 369, pp. 571-574.
Kaushansky, et al., Nature, Jun. 16, 1994, vol. 369, pp. 568-571.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, p. 127.
Greene, "Protective Groups in Organic Synthesis", 1981, Table of Contents.
Methia, et al., Blood, 1993, vol. 82, No. 5, pp. 1395-1401.
Yamazaki, et al., Japn. J. Toxicol. Environ. Health, 1994, vol. 94, No. 5, pp. 448-453.
Duffin, et al., J. of the Chem. Soc., 1954, pp. 408-441.
King, et al., Scand. J. of Immunol., 1999, vol. 49, No. 2, pp. 184-192.
Konica Corp. Derwent No. 92-077508/10, 1992.
Mitsubishi Pharma Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
Minssen-Guette, et al., Bulletin De La Societe Chimique De France, 1986, No. 5, pp. 2106-2110.
European Search Report dated Feb. 11, 2008 P51352EP.
Bussel, et al., Seminars in Hematology, 2000, vol. 37, pp. 1-49 (whole journal). see ids #7.
People's Republic of China, Office Action, dated Mar. 17, 2006.
CAS Online Registry No. 496775-62-3, Mar. 2002.
Asco Poster, Jun. 2006.
E.D. Derilus, GSK Clinical Disclosure; SB-497115 (Oral Thrombopoietin Receptor Agonist) Versus Placebo in Adult Cancer Patients Receiving Chemotherapy. www.clinicaltrials.gov; Feb. 1, 2005.
GSK Study Director, SB-497115 (Oral Thrombopoietin Receptor Agonist) Versus Placebo in Adults With Thrombocytopenia Due to Hepatitis C. www.clinicaltrials.gov; May 13, 2005.
E.D. Derilus, GSK Clinical Disclosure; EXTEND (Eltrombopag Extended Dosing Study) www.clinicaltrials.gov; Jul. 10, 2006.
E.D. Derilus, GSK Clinical Disclosure; (Oral Thrombopoietin Receptor Agonist) Versus Placebo in Adults With Refractory Immune Thrombocytopenic Purpura (ITP). www.clinicaltrials.gov; Feb. 1, 2005.
GSK Study Director, Study of SB-497115 in Healthy Subjects and Subjects With Mild, Moderate or Severe Renal Impairment. www.clinicaltrials.gov Mar. 1, 2007.
E.D. Derilus, GSK Clinical Disclosure; Repeated Exposure to Eltrombopag in Adults With Idiopathic Thrombocytopenic Purpura (REPEAT); www.clinicaltrials.gov Jan. 17, 2007.
GSK Study Director; RAISE: Randomized Placebo-Controlled idiopathic Thrombocytopenic Purpura (ITP) Study With Eltrombopag. www.clinicaltrials.gov Aug. 29, 2006.
E.D. Derilus, GSK Clinical Disclosure;Study of Eltrmbopag in Healthy Subjects and Volunteers With Mild, Moderate or Severe Hepatic Impairment. www.clinicaltrials.gov Jul. 28, 2006.

* cited by examiner

3'-[(2Z)-[1-(3,4-DIMETHYLPHENYL)-1,5-DIHYDRO-3-METHYL-5-OXO-4H-PYRAZOL-4-YLIDENE]HYDRAZINO]-2'-HYDROXY-[1,1'-BIPHENYL]-3-CARBOXYLIC ACID BIS-(MONOETHANOLAMINE)

This application is a Continuation of International Application No. PCT/US2007/074918 filed Aug. 1, 2007, which claims the benefit of U.S. Provisional Application Nos. 60/947,731 filed Jul. 3, 2007 and 60/915,761 filed May 3, 2007.

FIELD OF THE INVENTION

The present invention relates to granules and solid oral pharmaceutical dosage forms, suitably tablets, suitably capsules, comprising 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) represented by the following formula (I) and hereinafter referred to as "eltrombopag olamine" or Compound B:

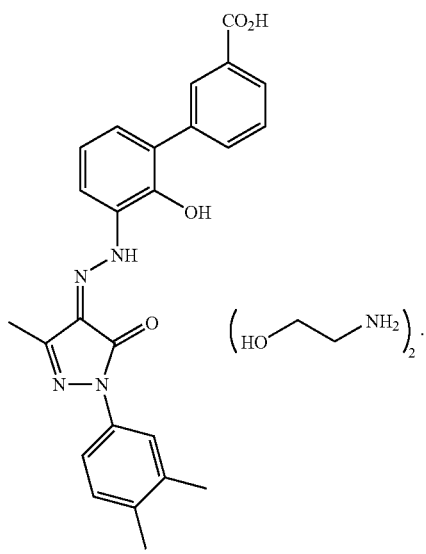

(Compound B)

BACKGROUND OF THE INVENTION

3'-{N'-[1-(3,4-dimethylphenyl)-3-methyl-5-oxo-1,5-dihydropyrazol-4-ylidene]hydrazino}-2'-hydroxybiphenyl-3-carboxylic acid (hereinafter Compound A) is a compound which is disclosed and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001; which has United States Publication Number US2004/0019190 A1, having a United States Publication date of Jan. 29, 2004; now U.S. Pat. No. 7,160,870, issued Jan. 9, 2007, the disclosure of which is hereby incorporated by reference.

The bis-(monoethanolamine) salt of this compound is disclosed (disclosed as 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, which also describes Compound A) in International Application No. PCT/US03/16255, having an International filing date of May 21, 2003; International Publication Number WO 03/098992 and an International Publication date of Dec. 4, 2003; which has United States Publication Number US2006/0178518 A1, having a United States Publication date of Aug. 10, 2006; the disclosure of which is hereby incorporated by reference.

Compound A is disclosed for the treatment of degenerative diseases/injuries in International Application No. PCT/US04/013468, having an International filing date of Apr. 29, 2004; International Publication Number WO 04/096154 and an International Publication date of Nov. 11, 2004; which has United States Publication Number US2007/0105824 A1, having a United States Publication date of May 10, 2007; the disclosure of which is hereby incorporated by reference.

Compositions that may contain Compound A and/or Compound B are disclosed in International Application No. PCT/US01/16863, International Application No. PCT/US03/16255 and International Application No. PCT/US04/013468.

Solid oral pharmaceutical dosage forms are popular and useful forms of medications for dispensing pharmaceutically active compounds. A variety of such forms are known, including tablets, capsules, pellets, lozenges, and powders.

However, the formulation of an acceptable solid oral pharmaceutical dosage form on a commercial scale is not always straightforward. The formula and process of manufacture must be such as to provide an integral solid dosage form that maintains its integrity until used. The solid dosage form must also possess acceptable dissolution and disintegration properties so as to provide the desired profile in use. Pharmaceutically active compounds with low solubility and/or that can react with commonly used excipients can present particular challenges in preparing high quality solid dosage forms, since the physical properties of the drug influence the properties of the solid dosage form. The formulator must balance the drug's unique properties with the properties of each excipient in order to prepare a safe, efficacious and easy to use solid dosage form.

Eltrombopag olamine presents the formulator with unique concerns when attempting to formulate this compound into a suitable solid oral pharmaceutical dosage form, suitably a tablet, suitably a capsule, with a desirable pharmacokinetic profile, particularly on a commercial scale. Such concerns include, but are not limited to; the tendency of the compound to form insoluble metal complexes when contacted with excipients that contain a coordinating metal, slow dissolution of the compound from solid dosage forms and the tendency of the compound to undergo a Maillard reaction when contacted with excipients that contain reducing sugars. Significant realization of these concerns will have an adverse effect on the in vivo administration of eltrombopag olamine.

It would be desirable to provide eltrombopag olamine in a solid oral pharmaceutical dosage form on a commercial scale with a desirable pharmacokinetic profile.

The present invention is directed to granules and solid oral pharmaceutical dosage forms that contain eltrombopag olamine, suitably the solid dosage form is a tablet, suitably the solid dosage form is a capsule, suitably these solid dosage forms are produced on a commercial scale.

SUMMARY OF THE INVENTION

The present invention relates to granules and solid oral pharmaceutical dosage forms comprising a therapeutically effective amount of eltrombopag olamine. The invention also relates to a process for making granules and solid oral pharmaceutical dosage forms comprising eltrombopag olamine.

Another aspect of this invention relates to granules and solid oral pharmaceutical dosage forms, suitably tablets, suitably capsules, comprising eltrombopag olamine that are formulated using diluents that are substantially free of reducing sugars, which as used herein and in the claims includes diluents that are free of reducing sugars, and that are substantially free of coordinating metals, which as used herein and in the claims includes diluents that are free of coordinating metals. Such granules and solid oral pharmaceutical dosage forms exhibit improved properties. Such improved properties help to ensure safe and effective treatment.

Another aspect of this invention relates to film coated pharmaceutical tablets comprising eltrombopag olamine, wherein the film coat contains no coordinating metals, or only an amount of coordinating metal approximately equal to or less than 0.025 parts of Compound B. Such tablets exhibit improved properties. Such improved properties help to ensure safe and effective treatment.

Another aspect of this invention relates to granules and solid oral pharmaceutical dosage forms comprising eltrombopag olamine that are formulated with a defined drug particle size range where about 90% of drug particle size is in the range of 10 to 90 microns. Such tablets exhibit improved properties. Such improved properties help to ensure safe and effective treatment.

Another aspect of this invention relates to granules and solid oral pharmaceutical dosage forms containing eltrombopag olamine comprising a high percentage of disintegrant, suitably an amount equal to or greater than 4%. Such tablets exhibit improved properties. Such improved properties help to ensure safe and effective treatment.

Another aspect of this invention relates to a method of treating thrombocytopenia, which method comprises administering to a subject in need thereof a therapeutically effective amount of granules or a solid oral pharmaceutical dosage form of the present invention.

Another aspect of this invention relates to a method of agonizing the TPO receptor, which method comprises administering to a subject in need thereof a therapeutically effective amount of granules or a solid oral pharmaceutical dosage form of the present invention.

Also included in the present invention are methods of co-administering granules or a solid oral pharmaceutical dosage form of the present invention with further active ingredients.

DETAILED DESCRIPTION OF THE INVENTION

Figure 1:
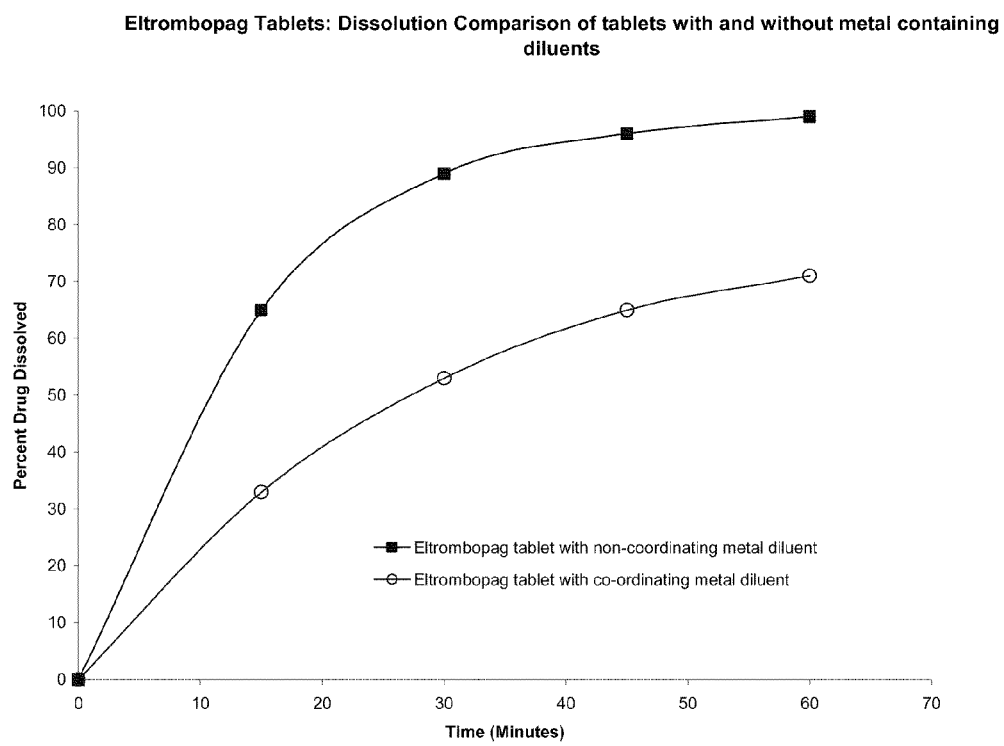
FIG. 1 depicts the dissolution comparison of tablets containing eltrombopag and a metal containing diluent with tablets containing eltrombopag and a non-metal containing diluent.

By the term "coordinating metal" and "coordinating metals" and derivatives thereof, as used herein is meant a metal or a metal containing excipient, suitably a diluent, or metal containing tablet coating material, which forms a complex, such as a chelate complex, in the presence of eltrombopag olamine. Examples of such metals include:

aluminum, calcium, copper, cobalt, gold, iron, magnesium, manganese and zinc.

By the term "reducing sugar" as used herein is meant a sugar or sugar containing excipient, suitably a diluent, which reacts with eltrombopag olamine to form a Maillard product when admixed together. Examples of such reducing sugars include:

lactose, maltose, glucose, arabinose and fructose.

The term Maillard reaction is well known in the art and is utilized herein as to its standard meaning. Generally, the term Maillard reaction is used herein to mean the reaction of a reducing sugar, as defined herein, in a formulation, suitably granules or solid dosage forms, with eltrombopag olamine that produces a pigment or pigments, suitably a brown pigment. The pigments are referred to herein as Maillard products. The production of such Maillard products is an indication of chemical instability.

As used herein, the term "improved properties" and derivatives thereof, contemplates several advantages to the pharmacokinetic profile of the in vivo release of Compound B from a formulation, suitably granules or a solid oral pharmaceutical dosage form, that utilizes an aspect of the present invention when compared to a formulation that does not utilize that aspect of the present invention, suitably the formulation is produced on a commercial scale, and will vary depending on the particular aspect of the invention being utilized. Examples of improved properties include: increased oral bioavailability, reduced formation of insoluble metal complexes, improved chemical stability, a consistent pharmacokinetic profile and a consistent dissolution rate.

As used herein, the term "drug" or "active ingredient" and derivatives thereof, means Compound B or eltrombopag olamine.

By the term "commercial scale" and derivatives thereof, as used herein is meant, preparation of a batch scale greater than about 20 kg of granulation mix, suitably greater than 50 kg, suitably greater than 75 kg or a batch size suitable to prepare at least about 50,000 tablets, suitably at least 75,000 tablets, suitably at least 100,000 tablets.

When indicating that the diluents for use herein and in the claims are substantially free of coordinating metals and/or that are substantially free of reducing sugars, it is contemplated that minor amounts, for example: about 5% or less, of the diluent component could contain a coordinating metal or metals and/or a reducing sugar or reducing sugars. In this aspect of the invention, it is believed that very minor amounts of coordinating metals and/or reducing sugars can be incorporated into the diluent component without adversely affecting tablet performance.

The term "effective amount" and derivatives thereof, means that amount of a drug or active ingredient that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "formulation" and derivatives thereof, unless otherwise defined refers to granules and/or solid oral pharmaceutical dosage forms of the invention that contain eltrombopag olamine.

By the term "co-administering" and derivatives thereof as used herein is meant either simultaneous administration or any manner of separate sequential administration of granules and/or a solid oral pharmaceutical dosage form of the present invention and a further active ingredient or ingredients, known to treat thrombocytopenia, including chemotherapyinduced thrombocytopenia and bone marrow transplantation and other conditions with depressed platelet production. The term further active ingredient or ingredients, as used herein, includes any compound or therapeutic agent known to or that demonstrates advantageous properties when administered with TPO or a TPO mimetic. Preferably, if the administration is not simultaneous, the compounds are administered in a close time proximity to each other. Furthermore, it does not matter if the compounds are administered in the same dosage form, e.g. one compound may be administered topically and another compound may be administered orally.

Examples of a further active ingredient or ingredients for use in combination with the presently invented formulations include but are not limited to:
chemoprotective or myeloprotective agents such as G-CSF, BB11000 (Clemons et al., *Breast Cancer Res. Treatment*, 1999, 57, 127), amifostine (Ethyol) (Fetscher et al., *Current Opinion in Hemat.*, 2000, 7, 255-60), SCF, IL-11, MCP-4, IL-1-beta, AcSDKP (Gaudron et al., *Stem Cells*, 1999, 17, 100-6), TNF-a, TGF-b, MIP-1a (Egger et al., *Bone Marrow Transpl.*, 1998, 22 (Suppl. 2), 34-35), and other molecules identified as having anti-apoptotic, survival or proliferative properties.

By the term "granules" and derivatives thereof, as used herein refers to formulated particles that comprise eltrombopag olamine, diluents that are substantially free of coordinating metals and/or that are substantially free of reducing sugars, and suitably also binders and/or lubricants and/or disintegrants such that the particles are suitable for utilization in preparing solid oral pharmaceutical dosage forms. It is also possible to administer the granules directly to a subject in need thereof as a medicament. However, it is anticipated that the granules are most appropriately utilized in the preparation of solid oral pharmaceutical dosage forms as indicated above.

By the term "solid oral pharmaceutical dosage form" and "solid dosage form" and derivatives thereof, as used herein refers to a final pharmaceutical preparation that comprises eltrombopag olamine, such tablets, capsules, pellets, lozenges and powders (including coated versions of any of such preparations) that are suitable for in vivo administration.

Suitably, the granules and solid oral pharmaceutical dosage forms of the present invention comprise eltrombopag olamine, a diluent (also known as filler or bulking agent), and suitably also a binder and/or a lubricant and/or a disintegrant. Those skilled in the art will recognize that a given material may provide one or more functions in the tablet formulation, although the material is usually included for a primary function. The percentages of diluent, binder, lubricant and disintegrant provided herein and in the claims are by weight of the tablet.

Diluents provide bulk, for example, in order to make the tablet a practical size for processing. Diluents may also aid processing, for example, by providing improved physical properties such as flow, compressibility, and tablet hardness. Because of the relatively high percentage of diluent and the amount of direct contact between the diluent and the active compound in the typical pharmaceutical formulation, the interaction of the diluent with the active compound is of particular concern to the formulator. Examples of diluents suitable for general use include: water-soluble fillers and water-insoluble fillers, such as calcium phosphate (e.g., di and tri basic, hydrated or anhydrous), calcium sulfate, calcium carbonate, magnesium carbonate, kaolin, spray dried or anhydrous lactose, cellulose (e.g., microcrystalline cellulose, powdered cellulose), pregelatinized starch, starch, lactitol, mannitol, sorbitol, maltodextrin, powdered sugar, compressible sugar, sucrose, dextrose, and inositol. The diluents that do not contain coordinating metals and diluents that are non-reducing sugars are suitable for tablets of the current invention. Suitable diluents for use in this invention include microcrystalline cellulose, powdered cellulose, pregelatinized starch, starch, lactitol, mannitol, sorbitol, and maltodextrin. Unsuitable diluents include calcium phosphate (e.g., di and tri basic, hydrated or anhydrous), calcium sulfate, calcium carbonate, magnesium carbonate, kaolin, and spray dried or anhydrous lactose. In one embodiment of the present invention, the diluent is composed of one or both of Mannitol and microcrystalline cellulose.

The granules and solid oral pharmaceutical dosage forms of the present invention typically comprise from about 25% to about 89%, of one or more diluents.

One aspect of the present invention comprises granules wherein the granules are formulated using a diluent or diluents that are substantially free of coordinating metals and/or that are substantially free of reducing sugars.

One aspect of the present invention comprises solid oral pharmaceutical dosage forms wherein the solid dosage forms are formulated using a diluent or diluents that are substantially free of coordinating metals and/or that are substantially free of reducing sugars.

One aspect of the present invention comprises pharmaceutical tablets, wherein the tablets are formulated using a diluent or diluents that are substantially free of coordinating metals and/or that are substantially free of reducing sugars.

One aspect of the present invention comprises pharmaceutical capsules, wherein the capsules are formulated using a diluent or diluents that are substantially free of coordinating metals and/or that are substantially free of reducing sugars.

Binders impart cohesive properties to the powdered material. Examples of binders suitable for use in the present invention include: starch (e.g., paste, pregelatinized, mucilage), gelatin, sugars (e.g., sucrose, glucose, dextrose, molasses, lactose, dextrin, xylitol, sorbitol), polymethacrylates, natural and synthetic gums (e.g., acacia, alginic acids and salts thereof such as sodium alginate, gum tragacanth, Irish moss extract, panwar gum, ghatti gum, guar gum, zein), cellulose derivatives [such as carboxymethyl cellulose and salts thereof, methyl cellulose (MC), hydroxypropyl methyl cellulose (HPMC), hydroxypropyl cellulose (HPC), hydroxyethyl cellulose (HEC) and ethyl cellulose (EC)], polyvinylpyrrolidone, Veegum, larch arabogalactan, polyethylene glycol, waxes, water, alcohol, magnesium aluminum silicate, and bentonites. In one embodiment of the present invention, the binder comprises polyvinylpyrrolidone (PVP).

The granules and solid oral pharmaceutical dosage forms of the present invention typically comprise up to about 8% binder. The formulations suitably comprise up to about 5%, suitably up to about 2% binder.

Lubricants are generally used to enhance processing, for example, to prevent adhesion of the formulation material to manufacturing equipment, reduce interparticle friction, improve rate of flow of the formulation, and/or assist ejection of the formulations from the manufacturing equipment. Examples of lubricants suitable for use in the present invention include: talc, stearates (e.g., magnesium stearate, calcium stearate, zinc stearate, palmitostearate), stearic acid, hydrogenated vegetable oils, glyceryl behanate, polyethylene glycol, ethylene oxide polymers (e.g., CARBOWAXes), liquid paraffin, sodium lauryl sulfate, magnesium lauryl sulfate, sodium oleate, sodium stearyl fumarate, DL-leucine, and silica derivatives (e.g., colloidal silicon dioxide, colloidal silica, pyrogenic silica, and hydrated sodium silicoaluminate). In one embodiment of the present invention, the lubricant comprises magnesium stearate.

The granules and solid oral pharmaceutical dosage forms of the present invention typically comprise up to about 2% lubricant. The formulations suitably comprise up to about 1.5%, suitably up to about 1% lubricant.

Disintegrants are employed to facilitate breakup or disintegration of the formulation after administration. Examples of disintegrants suitable for use in the present invention include: starches, celluloses, gums, crosslinked polymers, and effervescent agents, such as corn starch, potato starch, pregelatinized starch, modified corn starch, croscarmellose sodium, crospovidone, sodium starch glycolate, Veegum HV, methyl cellulose, microcrystalline cellulose, cellulose, modified cellulose gum (e.g., Ac-Di-Sol R), agar, bentonite, montmorillonite clay, natural sponge, cation exchange resins, ion exchange resins (e.g., polyacrin potassium), alginic acid and alginates, guar gum, citrus pulp, carboxymethylcellulose and salts thereof such as sodium lauryl sulfate, magnesium aluminum silicate, hydrous aluminum silicate, sodium bicarbonate in admixture with an acidulant such as tartaric acid or citric acid. In one embodiment of the present invention, the disintegrant is sodium starch glycolate.

The granules and solid oral pharmaceutical dosage forms of the present invention typically comprise an amount from 4% to about 12% disintegrant. The formulations suitably comprise from about 6% to about 10%, suitably from about 7% to 9% disintegrant.

The solid oral pharmaceutical dosage forms, suitably tablets, suitably capsules, of the present invention will typically be sized up to 1 gram, e.g., from about 0.01 gram to about 0.8 gram. These solid dosage forms typically comprise from about 5 mg to about 900 mg of eltrombopag olamine per dosage form. In suitable embodiments, the solid dosage forms comprise from about 5 to about 200 mg eltrombopag olamine (e.g., in an about 100-800 mg dosage form). Tablet formulations of the invention may have a variety of shapes, including diamond, modified capsule, modified oval, and hexagonal, and may optionally have a tilt.

Tablets

The choice of particular types and amounts of excipients, and tabletting technique employed depends on the further properties of eltrombopag olamine and the excipients, e.g., compressibility, flowability, particle size, compatibility, and density. The tablets may be prepared according to methods known in the art, including direct compression, dry granulation, fluid bed granulation, and wet granulation, and the type of excipients used will vary accordingly. It has been found that wet granulation is particularly suitable for providing high strength, low breakage tablets comprising relatively high concentrations of eltrombopag olamine (e.g., about 40% or more), on a scale suitable for commercial production. Suitable wet granulated tablets of the invention comprise granules comprising eltrombopag olamine and one or more of fillers, binders and disintegrants, wherein the granules are mixed with additional filler, binder, disintegrant and/or lubricant to form a compression mixture that is compressed to form tablets.

Included in the present invention are pharmaceutical compositions in tablet form, suitably prepared on a commercial scale, that comprise eltrombopag olamine, wherein the tablet is made by a wet granulation process using a diluent or diluents that are substantially free of coordinating metals and/or that are substantially free of reducing sugars. Also included in the present invention are such pharmaceutical compositions that contain a film coat, wherein the film coat contains no coordinating metals, or only an amount of coordinating metal approximately equal to or less than 0.025 parts of Compound B.

Also included in the present invention are pharmaceutical compositions that comprise eltrombopag olamine, wherein the tablet is made by a wet granulation process, suitably on a commercial scale, using a diluent or diluents that are substantially free of coordinating metals and/or that are substantially free of reducing sugars, and about 90% of the eltrombopag olamine particles have a particle size greater than 10 micron but less than 90 micron.

Also included in the present invention are pharmaceutical compositions that comprise eltrombopag olamine, wherein the tablet is made by a wet granulation process, suitably on a commercial scale, using a diluent or diluents that are substantially free of coordinating metals and/or that are substantially free of reducing sugars, and about 90% of the eltrombopag olamine particles have a particle size greater than 10 micron but less than 90 micron, suitably greater than 20 micron but less than 50 micron.

Also included in the present invention are pharmaceutical compositions that comprise eltrombopag olamine, wherein the tablet is made by a wet granulation process, suitably on a commercial scale, using a diluent or diluents that are substantially free of coordinating metals and/or that are substantially free of reducing sugars, and about 50% of the eltrombopag olamine particles have a particle size greater than 5 micron but less than 50 micron, suitably greater than 5 micron but less than 20 micron.

In one embodiment of the present invention, the tablets of the present invention comprise:
(i) from about 2% to about 65% eltrombopag olamine;
(ii) from about 25% to about 89% of diluent;
(iii) up to about 8% binder, suitably up to about 5%, suitably up to about 4%;
(iv) up to about 2% lubricant, suitably up to about 1.5%, suitably up to about 1%; and
(v) from 4% to about 12% disintegrant, suitably 6% to 10%, suitably from 7% to 9%.

Suitable wet granulated tablets comprise, by weight of the tablet, from about 10% to about 95% of eltrombopag olamine active intragranules and from about 5% to about 90% of external excipients; wherein the eltrombopag olamine active intragranules comprise, by weight of the intragranules:
(i) from about 2% to about 88% eltrombopag olamine;
(ii) from about 10% to about 96% diluent;
(iii) from about 2% to about 5% binder; and
(iv) optionally from 0% to about 4% disintegrant;
and wherein the external excipients comprise, by weight of the tablet:
(i) from 0% to about 70% diluent;
(ii) from about 0.25% to about 2%, suitably from about 0.25% to about 1.25% lubricant; and
(iii) from 4% to about 10% disintegrant.

In the foregoing embodiments, the diluent is suitably a combination of mannitol and microcrystalline cellulose, the non-reducing sugar is suitably mannitol, the binder is suitably polyvinylpyrolidone, the lubricant is suitably magnesium stearate, and the disintegrant is suitably sodium starch glycolate. Suitably, the intragranule filler is a mixture of mannitol and microcrystalline cellulose and the external filler is microcrystalline cellulose.

In one embodiment of the current invention, tablets are coated with a film coat formed from an aqueous film coat composition. Aqueous film coat compositions suitable for use in the present invention comprise a film-forming polymer, water as a vehicle, and optionally one or more adjuvants such as are known in the film-coating art. When the film coat contains a coordinating metal, as used herein, the amount of coordinating metal is approximately equal to or less than 0.025 parts of Compound B.

The film-forming polymer is selected to form coatings with mechanical properties (e.g., mechanical strength, flexibility) suitable to meet performance requirements, such as those required by the intended use environment (e.g., dissolution profile in gastrointestinal fluids), and/or use (e.g. solution viscosity). Examples of suitable film-forming polymers include cellulosic polymers (e.g., cellulose ethers such as HPMC, HPC, MC, EC, HEC, CAP, sodium ethyl cellulose sulfate, carboxymethyl cellulose and the like); polyvinylpyrolidone; zein; and acrylic polymers (e.g., methacrylic acid/methacrylic acid ester copolymers such as methacrylic acid/methylmethacrylate copolymers and the like). Cellulosic polymers are preferred in the present invention, especially cellulosic ethers and more especially HPMC and HPC. The polymers are typically provided in either aqueous or organic solvent based solutions or aqueous dispersions. However, the polymers may be provided in dry form, alone or in a powdery mixture with other components (e.g., a plasticizer and/or colorant), which is made into a solution or dispersion by the user by admixing with the aqueous vehicle.

The aqueous film coat composition further comprises water as a vehicle for the other components, to facilitate their delivery to the tablet surface. The vehicle may optionally further comprise one or more water soluble solvents, e.g., alcohols (e.g., methanol, isopropanol, propanol) and ketones (e.g., acetone). The skilled artisan can select appropriate vehicle components to provide good interaction between the film-forming polymer and the vehicle to ensure good film properties. In general, polymer-vehicle interaction is designed to yield maximum polymer chain extension to produce films having the greatest cohesive strength and thus mechanical properties. The components are also selected to provide good deposition of the film-forming polymer onto the tablet surface, such that a coherent and adherent film is achieved.

The aqueous film coating composition may optionally comprise one or more adjuvants known in the art, such as plasticizers, colorants, detackifiers, secondary film-forming polymers, flow aids, surfactants (e.g., to assist spreading), maltodextrin, and polydextrose.

Plasticizers provide flexibility to the film, which may reduce film cracking and improve adhesion to the tablet. Suitable plasticizers will generally have a high degree of compatibility with the film-forming polymer and sufficient permanence such that the coating properties are generally stable. Examples of suitable plasticizers include glycerin, propylene glycol, polyethylene glycols (e.g., molecular weight from 200 to 20,000, including Union Carbide's PEG 400, 4000, 6000, 8000, and 20,000), glycerin triacetate (aka triacetin), acetylated monoglyceride, citrate esters (e.g., triethyl citrate, acetyl triethyl citrate, tributyl citrate, acetyl tributyl citrate), phthalate esters (e.g., diethyl phthalate), mineral oil and hydrogenated glucose syrup. In one embodiment of the present invention, the plasticizer is chosen from polyethylene glycols, triacetin, propylene glycol, glycerin, and mixtures thereof.

The aqueous film coat composition suitably comprises one or more colorants. In addition to enhancing esthetic appeal, the colorant provides product identification. Suitable colorants include those approved and certified by the FDA, including FD&C and D&C approved dyes, lakes, and pigments, and titanium dioxide, provided that the film coat contains no coordinating metals, or only an amount of coordinating metal approximately equal to or less than 0.025 parts of Compound B.

Suitably, the colorant comprises one or more coloring agents selected from the group consisting of red iron oxides, red dyes and lakes, yellow iron oxides, yellow dyes and lakes, titanium dioxide, and indigo carmine. For example, the colorant may be selected to provide a light beige shade, for example consisting essentially of a) red iron oxide, red dye, and/or red lake, b) yellow iron oxide, yellow dye, and/or yellow lake, and c) titanium dioxide. Alternatively, the colorant may be selected to provide a pink shade (e.g., consisting essentially of titanium dioxide and red iron oxide, red dye and/or red lake); a light green shade (e.g., consisting essentially of yellow iron oxide, yellow dye and/or yellow lake, indigo carmine, and titanium dioxide); a light blue shade (e.g., consisting essentially of titanium dioxide and indigo carmine); or an orange shade (e.g., consisting of essentially of titanium dioxide and sunset yellow).

The above mentioned colorants that contain a coordinating metal are acceptable at a level approximately equal to or less than 0.025 parts of Compound B.

In suitable alternative embodiments, the aqueous film coating composition for use in the current invention comprises:
(i) a cellulosic film-forming polymer; and
(ii) a plasticizer.

Suitably, such compositions further comprise a colorant. Such compositions may optionally further comprise one or more additional adjuvants such as a detackifier, flow aid, surfactant, and secondary film-forming polymer.

Examples of optional detackifiers include lecithin, stearic acid, mineral oil, modified derivatized starch, tapioca dextrin, and polyethylene glycol. Examples of optional secondary film-forming polymers include sodium alginate, propylene glycol alginate, and polyvinylpyrrolidone. Examples of optional surfactants include dioctyl sodium sulfosuccinate and polysorbate 80. Examples of optional flow aids include talc, fumed silica, bentonite, hydrogenated vegetable oils, stearines, and waxes.

The aqueous film coat composition will typically comprise from about 5% to about 25%, suitably about 5% to about 20%, coating solids in the vehicle. In suitable embodiments, the solids typically comprise from about 25% to about 70%, suitably about 60% to about 70% film-forming polymer, about 5% to about 10%, suitably about 6% to about 8%, plasticizer, and about 20% to about 35% colorant, by weight.

A number of suitable aqueous film coating compositions are commercially available. The aqueous film coat composition may be provided in the form of a solution or dispersion. Alternatively, the composition may be provided in a dry form that can be combined with the vehicle components according to supplier instructions prior to coating the tablet. Suitably, aqueous film coating compositions are those commercially available from Colorcon, Inc. of West Point, Pa., under the trade name OPADRY and OPADRY II (nonlimiting examples include Opadry YS-1-7706-G white, Opadry Yellow 03B92357, Opadry Blue 03B90842). These compositions are available as dry film coating compositions that can be diluted in water shortly before use. OPADRY and OPADRY II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin).

The tablets are also suitably coated to provide a uniform coating without speckling. The tablets are typically coated to provide a dry tablet weight gain of from about 2 to about 5%, suitably about 3 to 4%.

The uncoated tablet cores are coated with the aqueous film coating composition by methods well known in the art using commercially available equipment (e.g., Thomas Accela-Cota, Vector Hi-Coater, Compu-Lab 36). In general, the process usually involves rolling or tumbling the tablets in a pan, or suspending the tablets on a cushion of air (fluidized bed), and intermittently or continuously (preferably continuously) spraying a fine mist of atomized droplets of the coating composition onto the tablets, the droplets wetting, spreading and coalescing on the surface of the tablets to form an adherent and coherent film coating. The tablets are typically heated to about 40 to 50° C., suitably about 45 to 50° C., e.g., by air having a temperature of up to about 75° C., suitably about 65 to 70° C.

Process of Making the Tablet

Pharmaceutical tablets of the invention that are wet-granulated can be prepared by a process comprising the steps of:
I) preparing the granules; which comprises the steps of:
  a) mixing together the dry materials comprising eltrombopag olamine, a diluent, a binder, and optionally a disintegrant for a time sufficient to homogenize the materials;
  b) adding a granulating fluid to the mixture of dry materials, preferably while mixing;
  c) mixing the granulating fluid with the mixture of dry materials for a granulating time sufficient to generally uniformly wet the dry materials, so as to form wet granules;
  d) wet-milling the wet granules;
  e) drying the wet-milled granules to form dry granules; and
  f) dry milling the dry granules to form granules of desired size;
II) preparing the tablet; which comprises the steps of:
  a) mixing the granules prepared in step I) f) with external excipients comprising a filler, a lubricant and a disintegrant for a time sufficient to homogenize the granules and external excipients; and
  b) compressing the mixture comprising the granules and external excipients to form a tablet.

Suitably, the tablets are further film-coated, especially aqueous film-coated.

In preparing wet-granulated granules, the dry materials may be mixed with suitable equipment such as known in the art (e.g., Niro-Fielder Blender/Granulator, Bear Varimixer, Key High Shear Mixer/Granulator) for a time sufficient to homogenize the materials, e.g., for about 3 minutes.

The granulating fluid is then added to the dry mixture, preferably while mixing. The granulating fluid is suitably water, although may alternatively be comprised of water in admixture with one or more of binders such as PVP and HPMC, from about 10 v/w % to about 30 v/w % of the granulating fluid, based on the total wet granulation mixture, is suitably used. The granulating fluid and dry materials may be mixed using suitable equipment such as known in the art (e.g., Niro-Fielder Blender/Granulator, Bear Varimixer, Key High Shear Mixer/Granulator) for a total time sufficient to generally uniformly wet the dry material so as to form wet granules, suitably for about 3 to about 15 minutes. Typically the fluid is added to the dry material with mixing over a period of about 1 to about 15 minutes, then the total batch is mixed for an additional time (post-granulating fluid-addition time), of about 0.5 minutes to about 6 minutes.

In a suitable embodiment, about 10 v/w % to about 30 v/w % granulating fluid and a post-granulating fluid-addition granulating time of about 6 minutes or less is used. Suitably, about 24 v/w % granulating fluid and a post-granulating fluid-addition granulating time of less than 3 minutes is used, e.g., about 2.5 minutes. Suitably, about 16 v/w % granulating fluid and a post-granulating fluid-addition granulating time of more than 2.5 minutes is used, e.g., about 4 minutes.

The wet granules are then wet-milled by methods such as are known in the art for providing a generally uniformly sized wet mass (such that the granules dry relatively evenly). Suitable wet-milling techniques may involve screening (e.g., manual screens), comminuting mills (such as a Co-mil, including but not limited to a 0.375" screen), or extruders.

The wet-milled granules are dried by methods such as are known in the art for providing generally uniform drying, to a low residual amount of granulating fluid (preferably about 0.5% to about 1.0%). Fluid bed dryers are suitable drying equipment.

The dried granules are then dry-milled using known methods to provide generally uniformly sized granules (unimodal distribution), suitably having a mean particle diameter of less than 240 microns (found to provide improved content uniformity). Suitable dry-milling equipment includes Co-mils, including but not limited to having a 0.094" screen.

Suitably the granules and the dry materials of the compression mix are generally unimodal in size distribution, in order to facilitate formation of a homogeneous mix and to mitigate possible segregation of the mix after blending. If necessary, the dry materials may be pre-screened to provide the desired particle size distribution. Screening of the lubricant may be particularly useful to deagglomerate the lubricant.

In preparing the compression mixture, the granules, filler, and disintegrant are mixed over a suitable period of time, about 5 to 15 minutes. Lubricant is then added and mixed for a suitable period of time, about 1 to 4 minutes. The mixture is then compressed into tablets using presses such as are known in the art (e.g., rotary tablet press).

It has been found that the above granulating fluid levels, granulating times, and excipients provide improved processing.

Capsules

The choice of particular types and amounts of excipients, and capsulation technique employed depends on the further properties of eltrombopag olamine and the excipients, e.g., compressibility, flowability, particle size, compatibility, and density. The capsules may be prepared according to methods known in the art, suitably filling a standard two piece hard gelatin capsule with eltrombopag olamine admixed with excipients, suitably filling a standard two piece hard gelatin capsule with granules prepared according to this invention, suitably on a scale suitable for commercial production. Suitable capsules of the invention comprise granules comprising eltrombopag olamine and one or more of fillers, binders and disintegrants, wherein the granules are mixed with additional filler, binder, disintegrant and/or lubricant to form a granular mixture that is filled into capsules.

Included in the present invention are pharmaceutical compositions in capsule form, suitably prepared on a commercial scale, that comprise eltrombopag olamine, wherein the capsule is made using a diluent or diluents that are substantially free of coordinating metals and/or that are substantially free of reducing sugars.

Also included in the present invention are pharmaceutical compositions that comprise eltrombopag olamine, wherein the capsule is made, suitably on a commercial scale, using a diluent or diluents that are substantially free of coordinating metals and/or that are substantially free of reducing sugars, and about 90% of the eltrombopag olamine particles have a particle size greater than 10 micron but less than 90 micron.

Also included in the present invention are pharmaceutical compositions that comprise eltrombopag olamine, wherein the capsule is made, suitably on a commercial scale, using a diluent or diluents that are substantially free of coordinating metals and/or that are substantially free of reducing sugars, and about 90% of the eltrombopag olamine particles have a particle size greater than 10 micron but less than 90 micron, suitably greater than 20 micron but less than 50 micron.

Also included in the present invention are pharmaceutical compositions that comprise eltrombopag olamine, wherein the capsule is made, suitably on a commercial scale, using a diluent or diluents that are substantially free of coordinating metals and/or that are substantially free of reducing sugars, and about 50% of the eltrombopag olamine particles have a particle size greater than 5 micron but less than 50 micron, suitably greater than 5 micron but less than 20 micron.

The invented granules and solid oral pharmaceutical dosage forms may be administered in therapeutically effective amounts to treat or prevent a disease state, e.g., as described in the above referenced International Applications Nos. PCT/US01/16863, PCT/US03/16255 and PCT/US04/013468, the disclosures of which are herein incorporated by reference. It will be recognized by one of skill in the art that the optimal quantity and spacing of individual dosages of eltrombopag olamine formulations of the invention will be determined by the nature and extent of the condition being treated and the particular patient being treated, and that such optimums can be determined by conventional techniques. It will also be appreciated by one of skill in the art that the optimal course of treatment, i.e., the number of doses of eltrombopag olamine given per day for a defined number of days, can be ascertained by those skilled in the art using conventional course of treatment determination tests.

A method of this invention of inducing TPO agonist activity in humans comprises administering to a subject in need of such activity a therapeutically effective amount of a solid oral pharmaceutical dosage form of the present invention.

The invention also provides for the use of eltrombopag olamine in the manufacture of a solid oral pharmaceutical dosage form of the present invention.

The invention also provides for the use of eltrombopag olamine in the manufacture of a solid oral pharmaceutical dosage form of the present invention for use in enhancing platelet production.

The invention also provides for the use of eltrombopag olamine in the manufacture of a solid oral pharmaceutical dosage form of the present invention for use in treating thrombocytopenia.

The invention also provides for a solid oral pharmaceutical dosage form for use as a TPO mimetic which comprises eltrombopag olamine and a pharmaceutically acceptable carrier of the present invention.

The invention also provides for a solid oral pharmaceutical dosage form for use in the treatment of thrombocytopenia which comprises eltrombopag olamine and a pharmaceutically acceptable carrier of the present invention.

The invention also provides for a solid oral pharmaceutical dosage form for use in enhancing platelet production which comprises eltrombopag olamine and a pharmaceutically acceptable carrier of the present invention.

The invention also provides a process for preparing solid oral pharmaceutical dosage forms containing a diluent or diluents that are substantially free of coordinating metals and/or that are substantially free of reducing sugars and a therapeutically effective amount of eltrombopag olamine, which process comprises bringing eltrombopag olamine into association with the diluent or diluents.

No unacceptable toxicological effects are expected when the compound of the invention is administered in accordance with the present invention.

Without further elaboration, it is believed that one skilled in the art can, using the preceding description, utilize the present invention to its fullest extent. The following Examples, therefore, are to be construed as merely illustrative and not a limitation of the scope of the present invention.

All the excipients utilized herein are standard pharmaceutical grade excipients available from numerous manufacturers well known to those in the art.

EXAMPLES

Examples 1 to 7

Tablet Preparation

Wet granulated, tablets comprising eltrombopag olamine and the ingredients in Table 1 were prepared.

TABLE 1

| Component/Tablet Strength | 12.5 mg | 25 mg | 25 mg | 50 mg | 50 mg | 75 mg | 100 mg |
|---|---|---|---|---|---|---|---|
| Granules 40% Drug-loaded | (39.9) | (79.7) | (79.7) | (159.4) | (159.4) | (239.1) | (318.8) |
| eltrombopag olamine, milled | 15.95 | 31.9 | 31.9 | 63.8 | 63.8 | 95.7 | 127.6 |
| Microcrystalline cellulose | 7.45 | 14.9 | 14.9 | 29.8 | 29.8 | 44.7 | 59.6 |
| Mannitol | 14.9 | 29.7 | 29.7 | 59.5 | 59.5 | 89.2 | 118.9 |
| Povidone | 1.6 | 3.2 | 3.2 | 6.4 | 6.4 | 9.6 | 12.8 |
| Purified water | — | — | — | — | | | |
| Extra-granular components | | | | | | | |
| Microcrystalline cellulose | 119.4 | 238.8 | 238.8 | 159.1 | 159.1 | 79.3 | NA |
| Sodium starch glycolate | 14.0 | 28.0 | 28.0 | 28.0 | 28.0 | 28.0 | 27.6 |
| Magnesium Stearate | 1.75 | 3.5 | 3.5 | 3.5 | 3.5 | 3.5 | 3.5 |

TABLE 1-continued

| Component/Tablet Strength | 12.5 mg | 25 mg | 25 mg | 50 mg | 50 mg | 75 mg | 100 mg |
|---|---|---|---|---|---|---|---|
| Film-coating components | | | | | | | |
| Purified water | | — | — | — | — | | |
| Opadry ® white | 8.9 | | 14.0 | | | 14.0 | 14.0 |
| Opadry Orange | | 14.0 | | | | | |
| Opadry Brown | | | | | 14.0 | | |
| Opadry Blue | | | | 14.0 | | | |
| Total tablet weight (mg/tablet) | 183.9 | 364 | 364 | 364 | 364 | 364 | 364 |

Granules were prepared by separately weighing and screening mannitol, microcrystalline cellulose and povidone.

As a general procedure, the ingredients were blended with the active ingredient and then wet-granulated (in a high-shear wet-granulator) with purified water. The wet-granule mass was wet-milled, then dried in a fluid-bed dryer and the dried granules were milled.

Then extragranular ingredients (microcrystalline cellulose, if needed, and sodium starch glycolate) were separately weighed, screened and blended with the granules. Magnesium stearate was added and blended with the mixture. The blend was compressed and the tablet cores were then film coated. The tablets were film coated with an aqueous suspension of OPADRY film coating preparation.

Example 8

Tablet Preparation

Eltrombopag olamine tablets containing diluents with the coordinating metal calcium phosphate dibasic anhydrous were manufactured in a similar manner as described above. Tablet composition for the tablet coordinating metal diluent is provided in table 2.

TABLE 2

| Component/Tablet Strength | 50 mg |
|---|---|
| Granules 40% Drug-loaded | (159.4) |
| eltrombopag olamine, milled | 63.8 |
| Calcium Phopshate dibasic anhydrous | 89.3 |
| Povidone | 6.4 |
| Purified water | — |
| Extra-granular components | |
| Microcrystalline cellulose | 159.1 |
| Sodium starch glycolate | 28.0 |
| Magnesium Stearate | 3.5 |
| Film-coating components | |
| Purified water | — |
| Opadry ® white | 14.0 |
| Total tablet weight (mg/tablet) | 364 |

In FIG. 1, the tablet prepared with no coordinating metal diluent (indicated as "with non-coordinating metal diluent") is a eltrombopag 50 mg tablet generally prepared as described in Table 1 above and the tablet prepared with the coordinating metal diluent—Calcium Phopshate dibasic anhydrous—(indicated as "with co-ordinating metal diluent") is a eltrombopag 50 mg tablet generally prepared as described in Table 2 above. Dissolution comparison was performed using USP Apparatus II, 50 rpm, in phosphate buffer pH 6.8 containing 0.5% Tween 80.

Example 9

Figure 2:
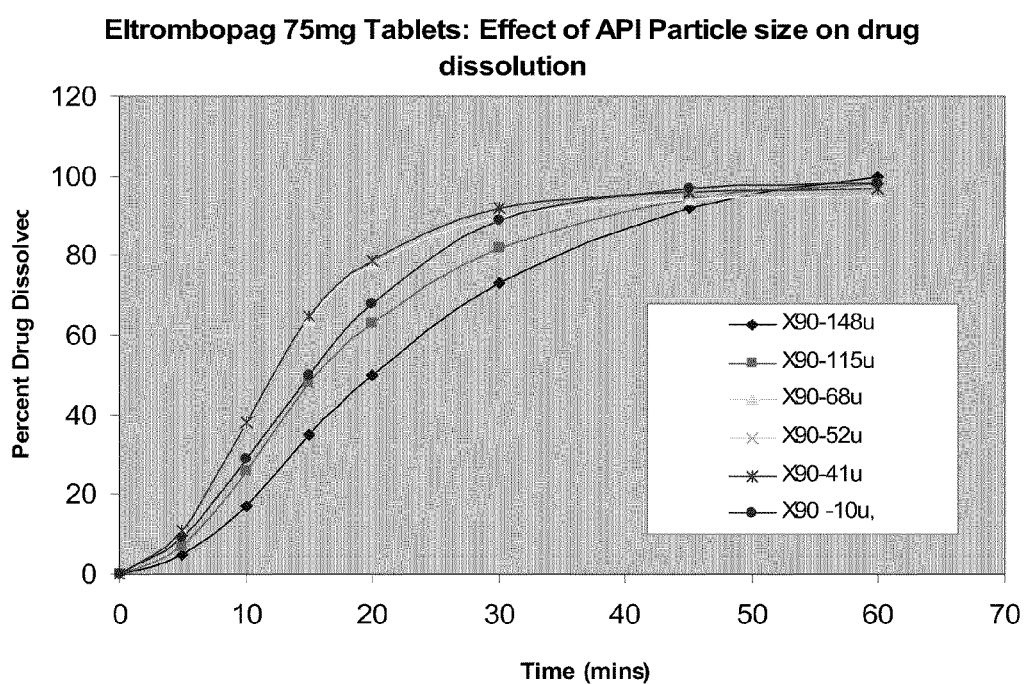
FIG. 2 depicts the effect of API particle size on the dissolution of eltrombopag from 75 mg tablets.

FIG. 2 depicts the effect of API particle size distribution on eltrombopag olamine dissolution. Eltrombopag olamine 75 mg tablets were generally prepared in the manner described in Example 5, using different particle sizes. The particle size refers to the particle size of the drug granules used in the formulation.

Dissolution comparison was performed using USP Apparatus II, 50 rpm, in phosphate buffer pH 6.8 containing 0.5% Tween 80.

What is claimed is:

1. A pharmaceutical tablet consisting essentially of:
    a) about 95.7 mg of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine);
    wherein,
    b) about 90% of the compound particles have a particle size of greater than 10 micron but less than 90 micron;
    c) the tablet is produced on a scale suitable to prepare at least about 50,000 tablets;
    d) the tablet contains from about 25% to about 89% by weight of one or more excipients selected from the group consisting of microcrystalline cellulose, powdered cellulose, pregelatinized starch, starch, lactitol, mannitol, sorbitol and maltodextrin;
    e) the tablet is film coated;
    f) the tablet contains a disintegrant in an amount from 4% to about 12% by weight;
    g) the tablet optionally contains a binder in an amount up to about 8% by weight; and
    h) the tablet optionally contains a lubricant in an amount up to about 2% by weight.

2. A pharmaceutical tablet according to claim 1 wherein: the tablet contains from about 25% to about 89% by weight of one or more excipients selected from the group consisting of microcrystalline cellulose and mannitol.

3. A process for preparing pharmaceutical tablets containing about 95.7 mg of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine), which process comprises the steps of;
    a) admixing:
        3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine), the compound wherein about 90% of the compound particles have a particle size of greater than 10 micron but less than 90 micron; one or more excipients selected from the group consisting of microcrystalline cellulose, powdered cellulose, pregelatinized starch, starch, lactitol, mannitol, sorbitol and maltodextrin; and
        further excipients;
        to form a mixture;

b) compressing the mixture into tablets; and c) applying a film coating to the tablets;

provided:

the process is carried out on a scale suitable to prepare at least about 50,000 tablets;

each tablet contains about 95.7 mg of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine); and each tablet contains from about 25% to about 89% by weight of one or more excipients selected from the group consisting of microcrystalline cellulose, powdered cellulose, pregelatinized starch, starch, lactitol, mannitol, sorbitol and maltodextrin;

each tablet contains a disintegrant in an amount from 4% to about 12% by weight;

each tablet optionally contains a binder in an amount up to about 8% by weight; and each tablet optionally contains a lubricant in an amount up to about 2% by weight.

4. A process according to claim 3 wherein:

each tablet contains from about 25% to about 89% by weight of one or more excipients selected from the group consisting of microcrystalline cellulose and mannitol.

5. A pharmaceutical tablet consisting essentially of:

a) about 95.7 mg of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine);

wherein, b) about 90% of the compound particles have a particle size of greater than 10 micron but less than 90 micron;

c) the tablet contains from about 25% to about 89% by weight of one or more excipients selected from the group consisting of microcrystalline cellulose, powdered cellulose, pregelatinized starch, starch, lactitol, mannitol, sorbitol and maltodextrin;

d) the tablet is film coated;

e) the tablet contains a disintegrant in an amount from 4% to about 12% by weight;

f) the tablet optionally contains a binder in an amount up to about 8% by weight; and g) the tablet optionally contains a lubricant in an amount up to about 2% by weight.

6. A pharmaceutical tablet according to claim 5 wherein:

the tablet contains from about 25% to about 89% by weight of one or more excipients selected from the group consisting of microcrystalline cellulose and mannitol.

7. A process for preparing pharmaceutical tablets containing about 95.7 mg of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine), which process comprises the steps of;

a) admixing:

the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine), wherein about 90% of the compound particles have a particle size of greater than 10 micron but less than 90 micron; one or more excipients selected from the group consisting of microcrystalline cellulose, powdered cellulose, pregelatinized starch, starch, lactitol, mannitol, sorbitol and maltodextrin; and further excipients;

to forth a mixture;

b) compressing the mixture into tablets; and c) applying a film coating to the tablets;

provided:

each tablet contains about 95.7 mg of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine); and each tablet contains from about 25% to about 89% by weight of one or more excipients selected from the group consisting of microcrystalline cellulose, powdered cellulose, pregelatinized starch, starch, lactitol, mannitol, sorbitol and maltodextrin;

each tablet contains a disintegrant in an amount from 4% to about 12% by weight;

each tablet optionally contains a binder in an amount up to about 8% by weight; and each tablet optionally contains a lubricant in an amount up to about 2% by weight.

8. A process according to claim 7 wherein:

each tablet contains from about 25% to about 89% by weight of one or more excipients selected from the group consisting of microcrystalline cellulose and mannitol.

9. A method of treating thrombocytopenia in a human in need thereof which comprises administering to such human a therapeutically effective amount of a pharmaceutical tablet according to claim 1.

10. A method of treating thrombocytopenia in a human in need thereof which comprises administering to such human a therapeutically effective amount of a pharmaceutical tablet according to claim 2.

11. A method of treating thrombocytopenia in a human in need thereof which comprises administering to such human a therapeutically effective amount of a pharmaceutical tablet according to claim 5.

12. A method of treating thrombocytopenia in a human in need thereof which comprises administering to such human a therapeutically effective amount of a pharmaceutical tablet according to claim 6.

* * * * *